United States Patent [19]

Besecke et al.

[11] Patent Number: 4,675,442
[45] Date of Patent: Jun. 23, 1987

[54] METHOD OF MAKING METHACRYLAMIDES

[75] Inventors: Siegmund Besecke, Seeheim-Jugenheim; Guenter Schroeder, Ober-Ramstadt, both of Fed. Rep. of Germany

[73] Assignee: Röhm GmbH, Darmstadt, Fed. Rep. of Germany

[21] Appl. No.: 709,343

[22] Filed: Mar. 6, 1985

Related U.S. Application Data

[63] Continuation of Ser. No. 384,477, Jun. 3, 1982, abandoned.

[30] Foreign Application Priority Data

Jun. 19, 1981 [DE] Fed. Rep. of Germany ....... 3123970

[51] Int. Cl.$^4$ .......................................... C07C 102/06
[52] U.S. Cl. ................... 564/135; 564/134; 564/137; 564/138; 564/141
[58] Field of Search ............... 564/134, 135, 137, 138, 564/141

[56] References Cited

U.S. PATENT DOCUMENTS

| | | | |
|---|---|---|---|
| 2,529,838 | 11/1950 | Erickson | 260/561 |
| 2,719,175 | 9/1955 | Coover et al. | 260/561 |
| 3,763,234 | 10/1973 | Brill | 564/137 X |
| 3,801,610 | 4/1974 | Werdehausen et al. | 260/404 |
| 3,816,483 | 6/1974 | Werdehausen et al. | 260/404 |
| 3,878,247 | 4/1975 | Moss et al. | 260/561 N |
| 3,907,893 | 9/1975 | Parker | 260/562 R |
| 3,945,970 | 3/1976 | Spoerke | 260/47 UA |
| 3,951,996 | 4/1976 | Stanley et al. | 564/141 X |
| 4,206,143 | 6/1980 | Wenzel et al. | 260/561 N |
| 4,228,102 | 10/1980 | Besecke et al. | 260/561 N |
| 4,321,411 | 3/1982 | Nakamura et al. | 564/135 |
| 4,549,017 | 10/1985 | McEntire et al. | 564/135 X |

FOREIGN PATENT DOCUMENTS

| | | |
|---|---|---|
| 2364059 | 7/1974 | Fed. Rep. of Germany . |
| 2502247 | 9/1977 | Fed. Rep. of Germany . |
| 2809102 | 9/1977 | Fed. Rep. of Germany . |
| 2816516 | 10/1979 | Fed. Rep. of Germany . |
| 3048020 | 7/1982 | Fed. Rep. of Germany . |
| 2097816 | 3/1972 | France . |
| 7900628 | 9/1979 | PCT Int'l Appl. . |
| 1312386 | 6/1973 | United Kingdom . |
| 2021101 | 11/1979 | United Kingdom . |

OTHER PUBLICATIONS

Riddle, Monomeric Acrylic Esters, Reinhold Publ. Corp., New York (1954), pp. 156–171.
Sugasawa et al., Reaction Index of Organic Syntheses, John Wiley & Sons, Inc. New York (1955), pp. 176, 177.
Holleman-Wiberg, Lehrbuch der Anorganischen Chemie, Walter de Gruyter, New York, 1985, pp. 239–240.
Olah, Friedel–Crafts and Related Reactions, vol. I., Interscience, New York, 1963, pp. 309–312.

Primary Examiner—Robert V. Hines
Attorney, Agent, or Firm—Curtis, Morris & Safford

[57] ABSTRACT

What is disclosed is a method for making an amide of acrylic acid or of methacrylic acid by the reaction of an alkyl ester of acrylic acid or of methacrylic acid with an amine at a temperature between 50° C. and 180° C., whereby the reaction with the amine is carried out in the presence of a catalytic amount of a compound of a metal of Group IVB of the periodic table of the elements or of a compound of lead, zinc, or tantalum.

7 Claims, No Drawings

METHOD OF MAKING METHACRYLAMIDES

This is a continuation of application Ser. No. 384,477 filed June 3, 1982 and now abandoned.

The present invention relates to a method for the preparation of an amide of acrylic or of methacrylic acid by the aminolysis of an ester of acrylic acid or of methacrylic acid, respectively, in the presence of a catalyst.

The aminolysis of esters, normally a relatively advantageous and straightforward process for the preparation of acid amides, becomes problematic if it involves the reaction of alpha, beta-unsaturated esters. In general, amines preferentially react by addition to such an activated double bond according to the "Michael addition". If acrylic acid esters or methacrylic acid esters are reacted with a molar amount of an amine, the corresponding beta-aminopropionic acid ester or beta-aminoisobutyric acid ester are obtained as the principal product in the temperature region below 180° C. The polymerization of the starting materials or of the end product, and addition to the double bond of the end product, are further reaction possibilities.

The undesired Michael addition of amines to esters of acrylic acid or of methacrylic acid is said to be excluded by the method of U.S. Pat. No. 2,719,175, in which the reaction is carried out in the gas phase at 300°–550° C. on solid catalysts such as vanadium-aluminum oxides with a dwell time of several seconds. However, uncontrolled side reactions and decomposition reactions occur at the high reaction temperatures so that the yields as a rule do not exceed 50 percent.

According to U.S. Pat. No. 2,529,838, N,N-dialkylacrylamides are obtained at somewhat lower temperatures (150°–400° C.) by the reaction of a lower acrylic acid ester with a long-chain secondary amine. In any event, the yield here appears also a rule not to exceed about 20 percent.

Thus, it has been sought to reach the desired goal in a two-step reaction.

According to the method of German Auslegeschrift Pat. No. 2,502,247, 1 mol of an acrylic acid ester or methacrylic acid ester is reacted in a first step at a temperature below 200° C. with 2 mols of a tertiary aminoalkylamine, whereby both Michael-addition and aminolysis proceed concurrently. In a second stage, the substituted 3-aminopropionamide obtained is heated to 180°–300° C. and the N-(tert.-aminoalkyl)-acrylamide is isolated from the reaction mixture by distillation.

Attempts to lead the reaction in the desired direction by the use of catalysts have also not been lacking. Thus, the preparation of aryl amides of methacrylic acid by the reaction of methyl methacrylate with (phenyl substituted) anilines in the presence of an alkali alcoholate is described in U.S. Pat. No. 3,945,970. U.S. Pat. No. 3,907,893 describes the preparation of amides by the reaction of unsaturated esters with aromatic amines in the presence of alkoxides or of amide bases.

From the published international PCT application 79 00 628, the preparation of amides of phenylene diamine by the aminolysis of methyl methacrylate in the presence of an alkali alcoholate is known.

German Offenlegungsschrift Pat. No. 28 09 102 teaches the preparation of acrylamides or of methacrylamides by the reaction of esters of the corresponding acids with an deficiency, up to a small excess, of an amine, with heating and under autogenous pressure in a homogeneous phase, preferably with proton catalysis.

A method for making N-substituted acrylamides or methacrylamides is known from German Offenlegungsschrift Pat. No. 28 16 516, according to which method an alkyl ester of acrylic acid or of methacrylic acid is reacted at a temperature between 50° C. and 180° C. with an aliphatic or aromatic amine in the presence of a catalytic amount of a dialkyltin oxide.

To be sure, the two last-mentioned patent publications particularly teach technically useful methods for the preparation of acrylic acid amides or of methacrylic acid amides. However, there nevertheless remains a requirement for a synthetic method which proceeds uniformly with good yields and in which, for example, the competitive Michael-addition to the double bond is suppressed as much as possible. Thus, the present invention has as its object an improved preparation of N-substituted amides of acrylic acid or of methacrylic acid proceeding from the esters of these acids, and particularly to simplify the method and to increase yields.

It has now been found that, starting with alkyl esters of acrylic acid or of methacrylic acids, N-substituted acrylamides or methacrylamides can be prepared in good yield and with high uniformity if the alkyl ester is reacted with a compound containing at least one -NH group, i.e. ammonia or, particularly, a primary or secondary aliphatic or aromatic amine, at a temperature between 50° C. and 180° C. in the presence of a compound of a metal of the IVth subgroup (i.e. Group IVB) of the periodic table of the elements and/or of a compound of the metals lead, tantalum, or zinc as a catalyst. The metals of said Group IVB are titanium, zirconium, and hafnium.

The method of the present invention is particularly suitable for the preparation of acid amides of the formula

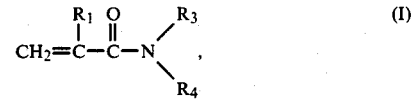

wherein $R_1$ is hydrogen or methyl; $R_3$, taken alone, is hydrogen, aralkyl, or is linear, branched, or cyclic saturated or unsaturated hydrocarbon having 1 to 18 carbon atoms or such aralkyl or hydrocarbon which is substituted; and $R_4$, taken alone, is hydrogen, aralkyl, or is linear, branched, or cyclic saturated or unsaturated hydrocarbon having 1 to 18 carbon atoms such aralkyl or hydrocarbon which is substituted, or is aryl or substituted aryl, or is alkenylcarboxamide of the formula

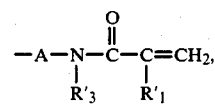

wherein $R'_3$ and $R'_1$ have the same definition as groups $R_3$ and $R_1$ but need not be identical with said latter groups. The term "aryl" as used herein designates aromatic hydrocarbon groups in general, e.g. phenyl ($C_6H_5$—), naphthyl ($C_{10}H_7$—), anthryl ($C_{14}H_9$—), and the like. "Aralkyl" encompasses compounds having such an aryl group substituted for a hydrogen atom on alkyl. $R_3$ and $R_4$, taken together with the nitrogen atom to which they are attached, may define a 5- or 6-membered heterocycle or such a heterocycle in which at least one further hetero atom, such as of nitrogen, oxygen, or sulfur, is present.

For such preparation, an ester of the formula

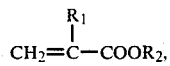 (II)

wherein $R_1$ has the above-identified meaning and $R_2$ is alkyl having 1 to 6 carbon atoms, preferably 1 or 2 carbon atoms, and ammonia or an amine of the formula

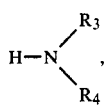 (III)

wherein $R_3$ and $R_4$ have the meanings described above, are reacted in the presence of a compound of a metal of Group IVB of the periodic table of the elements or a compound of lead, zinc, or tantalum as a catalyst, with the simultaneous formation of an alcohol, $R_2OH$, wherein $R_2$ has the aforementioned meaning.

As substituents which may be present on groups $R_3$ or $R_4$—as defined above—, carboxy, alkoxycarbonyl, (alkyl)-carbamoyl, sulfo, sulfonamido, and especially, N-carboxylamino, N-carboxyl-(N-alkyl)amino, nitro, and halo (alkyl)-amino groups should be particularly named. If the substituents include one or two alkyl groups, these groups are preferably such as have 1 to 6 carbon atoms. The carboxyl groups are preferably derived from $C_1$-$C_7$-carboxylic acids and especially from acrylic acid or methacrylic acid.

The amine of the general formula (III) can be represented in a narrower sense by the formula (III')

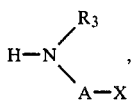 (III')

wherein $R_3$ has its earlier meaning and A is $-(CR_5R_6)_n-$ or is cyclohexylene, phenylene, diphenylene ether ($-C_6H_4OC_6H_4-$) or naphthylene. $R_5$ in turn is hydrogen or alkyl having 1 to 6 carbon atoms, $R_6$ is hydrogen or alkyl having 1 to 6 carbon atoms, X is hydrogen or a group $-COOH$, $-CONR_7R_8$, $-COOR_9$, $-SO_3H$, $-SO_2NR_7R_8$ or $-NR_7'R_8'$, and n is a whole number from 1 to 18. However, n can only stand for 1 if X does not have the meaning $-NR'_7R'_8$, i.e. amines of the formula

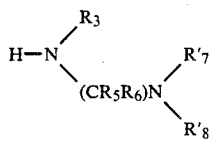

are excluded. $R_7$ and $R_8$ as well as $R'_7$ and $R'_8$ are independently selected from the group consisting of hydrogen or an alkyl group having from 1 to 6 carbon atoms. A together with X may form an allyl group. Finally, X may have the formula

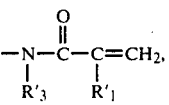

where, again, $R'_3$ and $R'_1$ have the same definition as groups $R_3$ and $R_1$ but need not be identical with such groups.

Preferably, $R_5$ and/or $R_6$ (to the extent that they represent alkyl groups) represent only one alkyl group having 1 to 6 carbon atoms per molecule and, otherwise, represent hydrogen.

The compounds of the general formula (III) encompass, for example, amino acids and their esters and amides, such as glycine and alanine; alkylene diamines, for example ethylene diamine, propylene diamine, hexamethylene diamine, phenylene diamine, neopentane diamine and dimethylaminoneopentane amine; as well as sarcosine. In case, within the scope of the present invention, such compounds of the general formula (III) are employed as have a second primary or secondary amino group, for example alkylene diamines, a reaction with two molecules of the alpha, beta-unsaturated ester of the general formula (II) is possible. This type of reaction forming a bis-amido compound is also intended to be covered by the present patent application.

As catalysts, compounds of titanium, zirconium, hafnium, lead, tantalum, and zinc, especially of tetravalent titanium and of tetravalent zirconium [cf. J. Bailar et al. in "Comprehensive Inorganic Chemistry" Vol. III, Pergamon Press, 1973] are especially mentioned. The alkoxides and aryloxides, as well as representatives having acid anions, particularly organic acids in a molecular complex, are preferred, in which case complex structures can be formed. Amides of the metals are also preferred.

As exemplary, metal compounds of the formula (V)

$$M^z(OR_{11})_z \quad (V)$$

should be mentioned, wherein M is a metal from the group consisting of titanium, zirconium, hafnium, lead, tantalum, and zinc, z is an integer corresponding to the valence of the metal, $R_{11}$ is an alkyl group preferably having 1 to 6 carbon atoms, and especially having 3 or 4 carbon atoms, or is an aryl group, particularly a phenyl or o-xylenyl group; or $R_{11}$ is the group

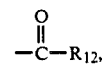

wherein $R_{12}$ represents a linear or branched, saturated or unsaturated aliphatic hydrocarbon or an aryl group; or $R_{11}$, together with the oxygen atom, represents an enolic system such as acetylacetone, for example, as well as amides formed analogously to the alkoxide. $R_{12}$ is preferably acryl or methacryl.

Titanium-IV-alkoxides, particularly those with methanol, propanol and butanol, and zirconium-IV-alkoxides, especially those with propanol and butanol, are particularly preferred. The tantalum-V-alkoxides, particularly those formed from ethanol, a propanol, or a butanol, should also be mentioned.

Additionally, compounds of the metals with acids, such as acrylic acid and/or methacrylic acid, for example, can be used. Also, the acetylacetonates, particularly those of zirconium and of titanium, should be mentioned.

Optionally, various types of substituents, e.g. (OR$_{11}$) can be in the molecular complex. A combination of the aforementioned catalysts with the catalysts recommended in DE-OS Pat. No. 28 16 516, i.e. with dialkyltin oxides of the formula $$OSn(R_{13})_2 \qquad (VI),$$

have proved to be particularly useful, wherein R$_{13}$ represents alkyl having 1 to 12 carbon atoms. The oxide in formula (VI) may be replaced by alkoxides or carboxylates which correspond to R$_{11}$.

The combination of compounds of titanium-IV, particularly of Ti-(OC$_3$H$_7$)$_4$, with the dialkyltin oxides of the formula (VI), particularly dibutyltin oxide, should be especially mentioned. Combined catalysts comprising the metal compounds of the formula (V) with the dialkyltin oxides of the formula (VI), wherein the compounds of (VI) are present in an amount of more than 50 mol percent, are particularly preferred, especially such combinations wherein the compounds of the formula (VI) make up from 60 to 90 mol percent of the mixture.

The metal compounds to be used according to the present invention, such as the compounds of the formula (V), are suitably used in catalytic amounts, for example in amounts of from 0.1 to 10 mol percent, preferably from 0.1 to 5 mol percent, calculated on the amine (III).

In general, the amine (III) is used in the present process in a deficient amount, e.g. from 0.05 to 0.5 mol of amine are used per mol of ester (II). The method can be carried out in a suitable solvent such as toluene, xylene, mesitylene, decalin, pyridine, or tetrachloroethylene. Preferably, however, it is carried out without any solvent.

The methods according to the present invention starting the methyl, ethyl, or butyl esters of acrylic acid or of methacrylic acid (R$_2$=methyl, ethyl, butyl) are particularly preferred, since they can be carried out on a technical scale and the alcohols which are cleaved in both reactions (R$_2$OH of IV) can be easily removed from the reaction mixture. The embodiment employing primary amines should be particularly mentioned, i.e. wherein R$_3$ represents hydrogen. Further, R$_4$ preferably stands for a substituent which imparts to the amine a boiling point of 80° C. or more. Further, reaction with an aminoalkyl amine, particularly with dialkylaminoalkyl amines such as dimethylaminopropyl amine, or with dimethylaminoneopentyl amine inter alia is of interest, as is reaction with an aralkyl amine, and an aromatic amine such as aniline, naphthylamine, and benzylamine, as well as reaction with an alkylene diamine to form a bis-acrylamide or bis-methacrylamide.

The reaction is more favorable if the boiling point of the amine (III), under the prevailing pressure conditions at which the process is carried out, is higher than the boiling point of the reaction mixture, since in this case the alcohol which is cleaved (IV) can be removed azeotropically with a portion of the ester starting material without any amount of the amine worth mentioning being simultaneously removed.

Formally, equal molar amounts of the reaction partners react to form the desired end product. However, in practice it has proved to be suitable to maintain the ester in excess throughout the reaction period. For example, the amine is gradually added under the reaction conditions to the ester which contains the catalyst. Advantageously, the process is carried out at boiling temperatures under atmospheric pressure, whereby a mixture of ester and of the cleaved alcohol are distilled off. The amount of ester reagent must, thus, either be chosen so large at the beginning that an excess of ester can be maintained throughout the course of the reaction, despite the losses due to distillation, or ester is constantly added together with the amine. It is less suitable to carry out the reaction under total reflux or beneath the boiling point, since then the cleaved alcohol cannot be removed from the reaction mixture. The alcohol-ester mixture which is distilled off can be worked-up in a manner known per se and the ester can again be used in a later batch.

In the method which has been described, the reaction temperatures are determined according to the boiling point of the ester employed and of the alcohol which is cleaved, and have a value between 50° C. and 180° C. As a rule, the sump temperature is at or above the boiling point of the ester, which is present in excess. For example, when methyl methacrylate is used, (R$_1$, R$_2$ equal methyl), the temperature is at or above 100° C. The temperature should suitably climb during the course of the reaction, for example by from 10° to 20° C., and possibly even more than that. The head temperature is below the boiling point, or at the boiling point, of the ester, since a mixture of ester and alcohol is distilled off during the course of the reaction. Toward the end of the reaction, if alcohol cleavage diminishes and the concentration of the ester in the reaction mixture decreases, the reaction temperature can be raised to 150° C. Higher temperatures encourage the formation of undesirable polymers.

The crude reaction product contains the N-substituted acrylamide in a yield of, usually, more than 80 percent, calculated on the amine introduced. As a rule, small amounts of the Michael adduct formed between the ester and the amine or from the substituted amide and the amine are obtained as by-products in the crude product. Although in many cases the crude product can be used directly for the preparation of polymerization products, as a rule a purification is carried out involving recrystallization or distillation. In this way, in most cases no fractionation column is necessary. If the distillation is carried out at reduced pressure and a boiling temperature between 150° and 200° C., the desired end product is obtained in high purity after a small initial fraction passes, and the by-products of the reaction are, for the most part, decomposed. In this mode of operation as described, (N-dimethylaminopropyl)methacrylamide can be obtained as a product which is 98 percent pure in a yield of about 95 percent of theory, calculated on the amount of dimethylaminopropyl amine employed.

It is suitable to carry out the reaction and to work-up the reaction mixture in the presence of a polymerization inhibitor, such as phenothiazine, in order to avoid losses due to polymerization.

A better understanding of the present invention and of its many advantages will be had by referring to the following specific Examples, given by way of illustration.

In Example 1, an embodiment involving benzylamine as the desired amine is given which embodiment can be generally employed.

EXAMPLE 1

3 mols of methyl methacrylate, 50 parts per million (ppm) of phenothiazine, 50 ppm of 4-methyl-2,6-di-tert-butylphenol (as a stabilizer/inhibitor), and 0.05 mol of the catalyst employed are heated to boiling in a 0.5 liter four-necked flask while a weak stream of air is introduced and the reaction mixture is stirred. Now, 0.5 mol of benzylamine was added dropwise over a period of one hour and the methanol/methylmethacrylate azeotrope which is formed was distilled off with a high reflux (bath temperature about 160° C.). Thereafter, the mixture was boiled for a further five hours while methanol/methylmethacrylate is circulated out of the system. The product yields of N-benzyl-methacrylamide, referred to the amine reagent, are reported in Table 1.

TABLE 1

| Example No. | Catalyst | Yield (% of theory) |
| --- | --- | --- |
| (Comparison) | no catalyst | — |
| 3 | titanium-IV-propoxide | 95 |
| 4 | zirconium-IV-butoxide | 61 |
| 5 | tantalum-V-ethoxide | 61 |
| 6 | lead-II-methacrylate | 45 |
| 7 | zirconium-IV-acetylacetonate | 41 |
| 8 | zinc-II-metnacrylate | 25 |

EXAMPLES 9–11

3 mols of methyl methacrylate were reacted under the standardized reaction conditions described for Example 1 with, respectively, 0.5 mol of hexamethylene diamine, 0.5 mol of dimethylaminopropyl amine, and with 0.5 mol of dimethylaminoneopentyl amine in the presence of 0.05 mol of titanium-IV-propylate. The following product yields, referred to the amine reagent, were obtained:

TABLE 2

| Example No. | Product | Yield (% of theory) |
| --- | --- | --- |
| 9 | N,N'—hexamethylene-dimethacrylamide | 48 |
| 10 | N—(dimethylaminopropyl)-methacrylamide | 94 |
| 11 | N—(dimethylaminoneopentyl)-methacrylamide | 88 |

EXAMPLES 12–14

Analogous to the standardized reaction conditions of Example 1, 3 mols of methyl methacrylate were reacted with 0.05 mol of aniline in the presence of a catalytic amount (altogether about 0.05 mol) of titanium-IV-propylate and dibutyltin oxide to form methacrylic acid anilide. In each case, the reaction time was six hours.

The yields are reported in Table 3.

TABLE 3

| Example No. | Catalyst of Titanium-IV-Propylate/ Dibutyltin Oxide (mol/mol) | Yield (% of theory) |
| --- | --- | --- |
| 12 | 0.6/0.4 | 74 |
| 13 | 0.4/0.6 | 81 |
| 14 | 0.2/0.8 | 81 |

Analogous to the standardized reaction conditions of Example 1 a series of acrylic or methacrylic esters were reacted. The reaction parameters and the results are given in Table 4.

TABLE 4

| Example No. | Ester of formula (II) $R_1$ | Ester of formula (II) $R_2$ | Mol used | Amine of formula (III) | Mol used (+) | Catalyst used | (% w/w) | Reaction time (h) | yield [%] |
| --- | --- | --- | --- | --- | --- | --- | --- | --- | --- |
| 15 | —CH$_3$ | —CH$_3$ | 8 | 4,4'-oxidianiline | (1) | dibutyl tin dimethacrylate / titanium-IV-methoxide | (3,0) / (1,7) | 16 | 91 |
| 16 | —H | —C$_4$H$_9$ | 4 | aniline | (1) | dibutyl tin oxide / titanium-IV-methoxide | (2,4) / (1,3) | 11 | 80 |
| 17 | —CH$_3$ | —C$_2$H$_5$ | 6 | ethyl ester of p-amino benzoic acid | (1) | dibutyl tin oxide / titanium-IV-methoxide | (2,6) / (1,3) | 24 | 75 |

+based on the ester of formula II.

What is claimed is:

1. A method for making an amide of acrylic acid or of methacrylic acid which comprises reacting an akyl ester of acrylic acid or of methacrylic acid with a primary or secondary aliphatic or aromatic amine at a temperature between 50° C. and 180° C. in the presence of a catalyst consisting essentially of 60 to 90 mol percent of a dialkyl tin oxide and 40 to 10 mol percent of a metal compound selected from the group consisting of alkoxides, aryloxides, carboxylates, and amides of titanium.

2. A method as in claim 1 wherein said amine is an aliphatic amine.

3. A method as in claim 1 wherein said amine is an aromatic amine.

4. A method as in claim 1 wherein said amine is a primary amine.

5. A method as in claim 1 wherein dibutyltin oxide is present in said catalyst and said metal compound is titanium-IV-alkoxide.

6. A method as in claim 1 wherein said alkyl ester is an alkyl methacrylate, whereby an amide of methacrylic acid is made.

7. A method as in claim 1 wherein said metal compound is a propoxide of titanium.

* * * * *